United States Patent [19]

Sherlock

[11] 4,125,612

[45] Nov. 14, 1978

[54] N-1-(P-BIPHENYLALKYL)PIPERAZINES AND THEIR USE AS ANTI-INFLAMMATORY AGENTS

[75] Inventor: Margaret H. Sherlock, Bloomfield, N.J.

[73] Assignee: Schering Corporation, Kenilworth, N.J.

[21] Appl. No.: 807,846

[22] Filed: Jun. 20, 1977

[51] Int. Cl.² .................. A61K 31/495; C07D 295/18; C07D 295/14; C07D 295/08

[52] U.S. Cl. ..................................... 424/250; 544/389; 544/391; 544/398; 544/399; 544/403

[58] Field of Search ...................... 260/268 R, 268 C; 424/250

[56] References Cited

PUBLICATIONS

E. Massarani et al., Chemical Abstracts, vol. 65, p. 7176 (1966).

Primary Examiner—Jose Tovar
Attorney, Agent, or Firm—Bruce M. Eisen; Raymond A. McDonald

[57] ABSTRACT

This invention relates to N-1(p-biphenylalkyl) piperazines, to the processes for making such compounds and to the use of such compounds as anti-inflammatory agents, particularly useful in the treatment of rheumatoid arthritis.

14 Claims, No Drawings

N-1-(P-BIPHENYLALKYL)PIPERAZINES AND THEIR USE AS ANTI-INFLAMMATORY AGENTS

This invention relates to compositions of matter classified in the art of chemistry as N-1-(p-biphenylalkyl)-piperazines and to the processes for making and using such compositions.

The invention sought to be patented in one of its composition of matter aspects resides in the chemical compounds 1-(X,Y-substituted-p-biphenylalkyl)-4-$R^1$-substituted piperazines wherein X is halogeno, trifluoromethyl or difluoromethyl, Y is halogeno, difluoromethyl, trifluoromethyl or hydrogen, and $R^1$ is hydrogen, formyl, carboalkoxy, hydroxyalkyl, alkoxyalkyl, cinnamyl, acyl or acyloxyalkyl, and the pharmaceutically acceptable acid addition salts thereof.

The invention sought to be patented in another of its composition of matter aspects resides in the concept of pharmaceutical dosage forms containing a novel 1-(X,Y-p-biphenylalkyl)-4-$R^1$-piperazine, either in the form of its free base or as pharmaceutically acceptable acid addition salt thereof, in admixture with pharmaceutical carrier suitable for enteral or parenteral administration.

The invention sought to be patented in one of its process aspects residing in the concept of administering to a mammal suffering from rheumatoid arthritis a therapeutically effective amount of an 1-(X,Y-p-biphenylalkyl)-4-$R^1$-piperazine of this invention, either as the free base or in the form of an acid addition salt thereof, in admixture with a pharmaceutically acceptable carrier.

More specifically, the tangible embodiments of the compositions of matter of this invention relate to those 1-(X,Y-p-biphenylalkyl)-4-$R^1$-piperazines having the structural formula:

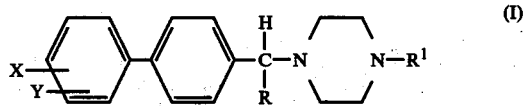

and the pharmaceutically acceptable acid addition salts thereof, wherein X is halogeno, difluoromethyl or trifluoromethyl, Y is hydrogen, halogeno, difluoromethyl or trifluoromethyl, R is lower alkyl, $R^1$ is hydrogen, formyl, carboalkoxy, hydroxyalkyl, alkoxyalkyl, cinnamyl, acyl or acyloxyalkyl.

The term "lower alkyl" includes those straight and branched chain saturated hydrocarbyl radicals having up to six carbon atoms, including isopropyl, butyl, hexyl, t-butyl, and preferably, methyl and ethyl. Halogeno includes chloro, bromo and iodo, and preferably, fluoro. When Y is hydrogen, it is preferred that the monosubstituted compounds bear the substituent at the 4' position and when disubstituted, it is preferred that the substituents be located at the 3',4'-positions, although disubstitution may also occur at the 2',4'-positions. In those instances wherein the $R^1$ substituent contains an acyl moiety, then that moiety is derived from those monobasic carboxylic acids having up to 14 carbon atoms. These radicals may be more conveniently represented as

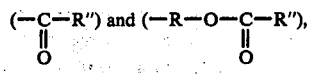

(i.e., acyl, and acyloxy alkyl, respectively) wherein R" is a straight, branched chain or cyclic alkyl moiety having up to 14 carbon atoms, and R is lower alkyl. Among the more suitable acyl moieties are those derived from such acids as acetic, propionic, butyric, hexanoic, cyclohexanoic, heptanoic, octanoic, 2-ethyl-heptanoic, 2,2-diethylbutyric, capric, lauric, tridecylic, myristic, palmitic, stearic, 2-nonenic, pivalic citronellic, undecylenic and oleic acids, as well as such other acids known for their prolonged action-inducing effects. Methoxy, ethoxy, isopropoxy and butyloxy are preferred alkoxy moieties (of the carboalkoxy and alkoxyalkyl radicals) although other straight and branched chain moieties having up to 6 carbon atoms are contemplated. Hydroxyethyl, hydroxypropyl and hydroxybutyl are preferred hydroxyalkyl radicals although other straight and branched chain radicals having up to 6 carbon atoms are contemplated.

In general, the compounds of this invention (I) may be prepared from appropriately X,Y-substituted biphenyl compounds (II) by a series of standard and well-known chemical transformations. In the first step of the synthesis appropriately X,Y-substituted biphenyl compounds are acylated utilizing conditions of the Friedel-Crafts reaction wherein the biphenyl compound is reacted with an alkanoyl halide in the presence of aliminum chloride to produce a biphenyl ketone (III). These biphenyl ketones are chemically reduced to the corresponding carbinols (IV) by reaction with a metallic hydride. Preferably the biphenyl ketones are reduced to the corresponding carbinol with sodium borohydride, but lithium aluminum hydride may also be employed. Alternatively, the biphenyl carbinols (IV) may be prepared using a Grignard reaction wherein an appropriate aldehyde is added to the magnesium halide complex formed by reacting a biphenyl halide with magnesium in an inert solvent such as tetrahydrofuran.

The biphenyl alkanols (IV) are converted to either biphenyl alkyl halides or to biphenyl alkyl sulfonate esters prior to the formation of the piperazine derivatives. The biphenyl alkyl halides are prepared by reacting the biphenyl alkanols with thionyl chloride or with an inorganic acid halide. Preferably thionyl chloride is heated, at reflux temperatures, with the biphenyl alkanol in an anhydrous solvent and the so-produced biphenyl alkyl halide is isolated and purified prior to its reaction with piperazine. When the biphenyl alkyl sulfonate esters are prepared, they need not be purified prior to reaction with the piperazine reactants. The preferred sulfonate ester derivatives are the tosylate and mesylate, such esters being prepared by standard techniques well known in the art.

As can be seen from the definition of the 1-(X,Y-p-biphenyl alkyl) -4-$R^1$ piperazines of this invention, the piperazine moiety can bear $R^1$ substituents such as hydrogen, formyl, carboalkoxy, hydroxyalkyl, alkoxyalkyl, cinnamyl, acyl and acyloxyalkyl. In those instances wherein the $R^1$ represents either hydrogen, formyl, carboalkoxy, hydroxyalkyl or acyl, the condensation reaction of the biphenyl alkyl halide (VI) or the biphenyl alkyl sulfonate ester (V) with the piperazine may be accomplished by using a piperazine already bearing such substitution. However, such compounds, as well as those compounds wherein the $R^1$ substituent is alkoxyalkyl, cinnamyl or acyloxyalkyl, are preferably produced by utilizing a finishing step after the biphenyl alkyl halide or sulfonate ester has been condensed with an otherwise unsubstituted piperazine. In either case, the alkyl halide is condensed with a piperazine by standard technique. In practice it is preferred to admix the reactants and allow the condensation to take place at room temperature over a period of several hours, although the condensation may be hastened at slightly elevated temperatures.

To prepare compounds wherein $R^1$ is alkoxyalkyl a 1(X,Y-p-biphenyl alkyl)-4-hydroxy alkyl piperazine is reacted upon with thionyl chloride to produce a chloride dihydrochloride reactive derivative which, when heated with a sodium alkoxide (eg. sodium methylate) the desired alkoxyalkyl derivative is prepared. Similarly, 1(X,Y-p-biphenyl alkyl) piperazine is heated with cinnamyl bromide to produce the desired compound. In producing the acyloxyalkyl derivatives, a (X,Y-p-biphenyl alkyl)-4-hydroxyalkyl piperazine is esterified by heating said hydroxyalkyl bearing compound with an acid anhydride in an anhydrous inert solvent.

The foregoing reactions may be schematically depicted as follows:

acids, e.g. hydrochloric, hydrobromic, nitric, sulfuric, or phosphoric acid, or organic acids, such as carboxylic or sulfonic acids, e.g. acetic, propionic glycolic malonic, succinic, maleic, hydroxymaleic, fumaric, malic, tartaric, citric, glucuronic, benzoic, salicylic, 4-aminosalicylic, 2-acetoxybenzoic, pamoic, nicotinic, isonicotinic, methane sulfonic, ethane sulfonic, ethane 1,2-disulfonic, 2-hydroxyethane sulfonic, benzene sulfonic, toluene sulfonic or naphthalene 2-sulfonic acid methionine, lysine, tryptophan or arginine. Other acid addition salts are useful as intermediates for the preparation of the pure parent compounds or in the manufacture of other salts, as well as for identification or characterization purposes. Addition salts primarily used for the latter are, for example, those with certain inorganic acids, e.g. perchloric, phosphotungstic, phosphomolybdic, chloroplatinic, or Reinecke acid or with acidic organic nitro compounds, e.g. picric, picrolonic or flavianic acid. The bases are converted into salts, the salts are separated and the bases liberated from the salts. In view of the close relationship between the free compounds and the compounds in the form of their salts, whenever a free compound is referred to in this context, a corresponding salt is also intended, provided such is possible and useful.

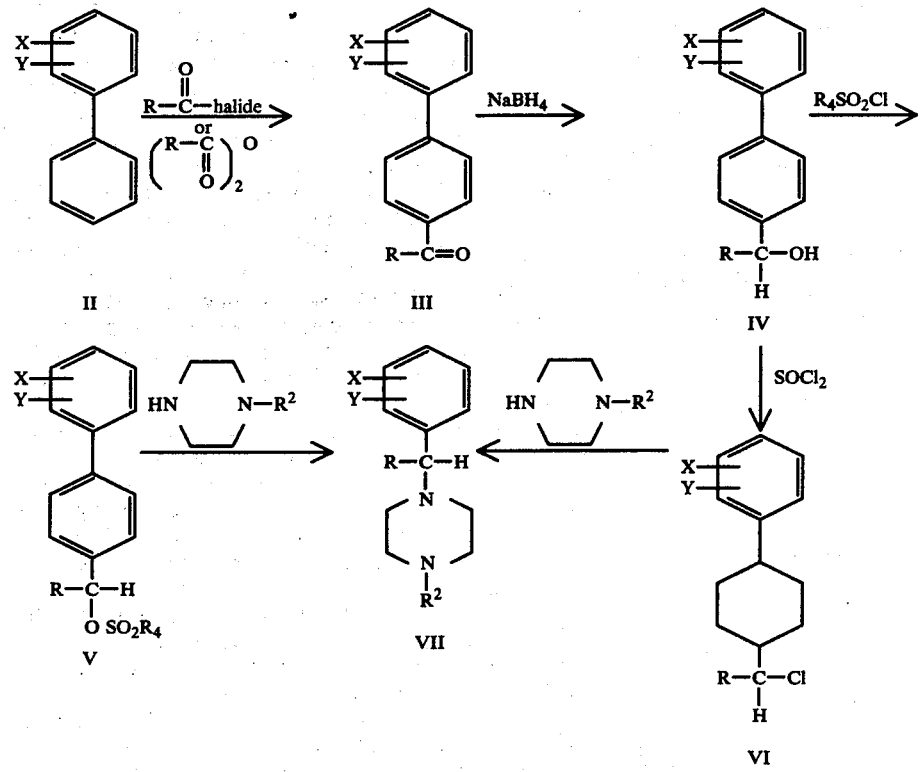

wherein X, Y and R are as defined hereinabove, $R^4$ is alkyl or tolyl, $R^2$ is hydrogen, formyl, carboalkoxy, hydroxyalkyl or acyl.

In some instances the free base of the compounds of this invention are produced in crystalline form which are suitable for use in pharmaceutical formulations. However, such compounds, in addition to those which do not readily crystallize, may be reacted upon to form acid addition salts. A free base of Formula I is converted into a salt thereof, by its treatment with an acid or an anion exchange preparation. Preferred salts are those of therapeutically useful acids, such as inorganic

PREPARATION OF KETONE INTERMEDIATES

EXAMPLE 1

1-(4'-Chloro[1,1']biphenyl-4-yl)ethanone

To a cooled, stirred suspension containing 154 gms. of anhydrous aluminum chloride, 800 ml. of carbon tetrachloride and 200 gms of p-chlorobiphenyl add (dropwise) 91 gms of acetyl chloride. When the reaction temperature of the mixture reaches 10° C., add 60 ml of methylene chloride and allow the reaction mixture to slowly reach room temperature. Stir the mixture overnight. Pour the resulting mixture into 1 liter of crushed ice and water containing 100 ml. of conc. hydrochloric acid. Separate the organic phase, dry over anhydrous sulfate, filter, concentrate, and triturate the solid residue with 600 ml. of hexane to yield 1-(4'chloro[1,1']biphenyl-4-yl) ethanone, m.p. 100°–101° C.

In a similar manner, the following biphenyl ketones are prepared:

1-(3',4'-dichloro[1,1']biphenyl-4-yl)ethanone,
1-(4'-chloro[1,1']biphenyl-4-yl)propanone,
1-(4'-chloro[1,1']biphenyl-4-yl)butanone,
1-(4'-chloro[1,1']biphenyl-4-yl)pentanone
1-(4'-chloro[1,1']biphenyl-4-yl)hexanone,
1-(4'-fluoro[1,1']biphenyl-4-yl)ethanone,
1-(2'-fluoro[1,1']biphenyl-4-yl)ethanone,
1-(3',4'difluoro[1,1']biphenyl-4-yl)ethanone,
1-(2',4'difluoro[1,1']biphenyl-4-yl)ethanone,
1-(4'-trifluoromethyl-[1,1']-biphenyl-4-yl)ethanone,
1-(4'-difluoromethyl-[1,1']-biphenyl-4-yl)ethanone

PREPARATION OF CARBINOL INTERMEDIATES

EXAMPLE 2

1-(4'-chloro[1,1']-biphenyl-4-yl)ethanol

To a stirred suspension of 222 gms of 1-(4'-chloro[1,1']-biphenyl-4-yl)ethanone in 1500 ml of methanol add in a portionwise fashion, 21 gms of sodium borohydride. Reflux and stir the mixture on a steam bath for 2 hours and stir at room temperature overnight. Concentrate the mixture to 500 ml, dilute with water, cool and filter the product to yield 238 gms of 1-(4'-chloro[1,1']biphenyl-4-yl)ethanol.

In a similar manner, the following biphenyl carbinols are prepared:

1-(4'-bromo-[1,1']-biphenyl-4-yl)-ethanol,
1-(4'-fluoro[1,1']-biphenyl-4-yl)-ethanol,
1-(2'-fluoro[1,1']-biphenyl-4-yl)-ethanol,
1-(4'-chloro[1,1']-biphenyl-4-yl)-propanol,
1-(4'-chloro[1,1']-biphenyl-4-yl)-butanol,
1-(4'-chloro[1,1']-biphenyl-4-yl)-pentanol,
1-(4'-chloro[1,1']-biphenyl-4-yl)-hexanol,
1-(3',4'-dichloro[1,1']-biphenyl-4-yl)-ethanol,
1-(3',4'-difluoro-[1,1']-biphenyl-4-yl)-ethanol,
1-(2',4'-difluoro-[1,1']-biphenyl-4-yl)-ethanol,
1-(4'trifluoromethyl-[1,1']-biphenyl-4-yl)-ethanol.

EXAMPLE 3

1-(4'-trifluoromethyl-[1,1']-biphenyl-4-yl)-ethanol

To a stirred suspension of 1.5 g of magnesium turnings in 10 ml of dry tetrahydrofuran, add a small amount of 4'-trifluoromethyl-4-bromo[1,1']biphenyl and a few drops of bromine. When the reaction is started, add (dropwise) a solution of 16 g of 4'-trifluoromethyl-4-bromo-[1,1']biphenyl in 50 ml of tetrahydrofuran at 50°–60° C. Heat the mixture for one hour, cool to 0° C., and slowly (dropwise) add 7 g of acetaldehyde. Stir the reaction mixture at room temperature for twenty hours. Work-up the reaction mixture following the procedure of example 2, and isolate the desired product by chromatography, m.p. 116°–117°.

PREPARATION OF CHLORIDES AND SULFONATES

EXAMPLE 4

4'-chloro-4-(1-chloroethyl)[1,1']-biphenyl

To a stirred suspension of 238 g of 1-(4'-chloro[1,1'λ]biphenyl-4-yl)ethanol in 2 liters of anhydrous benzene add 200 ml. of thionyl chloride over 40 minutes. With stirring, reflux the reaction mixture for 4 hours. Concentrate the reaction mixture and dissolve the resulting solid residue in 2 liters of methylene chloride. Wash the methylene chloride solution with three 500 ml portions of water, dry the resulting solution over sodium sulfate, concentrate, and triturate the solid residue with petroleum ether to yield 4'-chloro-4-(1-chloroethyl)[1,1']-biphenyl m.p. 100°–102° C.

In a similar manner, there is produced the following chlorides:

-4'-bromo-4-(1-chloroethyl)[1,1']-biphenyl,
-4'-fluoro-4-(1-chloroethyl[1,1']-biphenyl,
-2'-fluoro-4-(1-chloroethyl)[1,1']-biphenyl,
-4-chloro-4-(1-chloropropyl)[1,1']-biphenyl,
-4-chloro-4-(1-chlorobutyl)[1,1']-biphenyl,
-4-chloro-4-(1-chloropentyl)[1,1']-biphenyl,
-4'-chloro-4-(1-chlorohexyl)[1,1']-biphenyl,
-3',4'-dichloro-4-(1-chloroethyl)[1,1']-biphenyl,
-3',4'-difluoro-4-(1-chloroethyl[1,1']-biphenyl,
-2',4'-difluoro-4-(1-chloroethyl)[1,1']-biphenyl,
-4'-difluoromethyl-4-(1-chloroethyl)[1,1']-biphenyl.

EXAMPLE 5

4'-fluoro-4-(1-methanesulfonoxyethyl)-[1,1']-biphenyl

To a stirred solution of 18.2 g of 1-(4'fluoro[1,1'λ]biphenyl-4-yl)ethanol and 9.3 g of triethylamine in 500 ml of anhydrous benzene add, in a dropwise fashion, 10.4 g of methane sulfonyl chloride in 10 ml of anhydrous benzene. Stir the reaction mixture for one hour at room temperature, filter off the triethylamine hydrochloride and concentrate the filtrate, in vacuo, at 30°. The crude mesylate was not purified further but used directly in subsequent reactions with the substituted piperazines.

In a similar manner the following mesylates may be prepared:

4'-bromo-4-(1-methanesulfonoxyethyl)-[1,1']-biphenyl,
4'-fluoro-4-(1-methanesulfonoxyethyl)-[1,1']-biphenyl,
2'-fluoro-4-(1-methanesulfonoxyethyl)-[1,1']-biphenyl,
4'-chloro-4(1-methanesulfonoxypropyl)-[1,1']-biphenyl
4'-chloro-4(1-methanesulfonoxybutyl)-[1,1']-biphenyl,
4'-chloro-4(1-methanesulfonoxypentyl)-[1,1']-biphenyl,
4'-chloro-4(1-methanesulfonoxyhexyl)-[1,1']-biphenyl,
3',4'-dichloro-4-(1-methanesulfonoxyethyl)-[1,1']-biphenyl,
3',4'-difluoro-4-(1-methanesulfonoxyethyl)-[1,1']-biphenyl,
2',4'-difluoro-4-(1-methanesulfonoxyethyl)-[1,1']-biphenyl,
4'-difluoromethyl-4-(1-methanesulfonoxyethyl)-[1,1']-biphenyl,
4'-trifluoromethyl-4-(1-methanesulfonoxyethyl)-[1,1']-biphenyl.

PREPARATION OF FINAL COMPOUNDS

EXAMPLE 5

1-[1-(4'-chloro[1,1']biphenyl-4-yl)ethyl]piperazine

While stirring, reflux a solution of 90g of anhydrous piperazine, 52g of 4'-chloro-4-(1-chloroethyl)[1,1'λ]biphenyl and 700 ml of anhydrous benzene for 24 hours. Add 300 ml. of water to the reaction mixture, separate the benzene layer and extract with dilute hydrochloric acid. Separate and filter the acidic aqueous phase, basify the filtrate with dilute sodium hydroxide and extract with methylene chloride. Dry the organic extract, concentrate and triturate the resulting solid residue with petroleum ether. Filter and recrystallize the product from methanol to yield 1-[1-(4'-chloro[1,1'λ]biphenyl-4-yl)ethyl] piperazine m.p. 164°–165° C. The dihydrochloride salt (from methanol as hemihydrate) has a m.p. 263°–264°.

EXAMPLE 6

1[1-(4'-chloro[1,1']biphenyl-4-yl)propyl]piperazine

Reflux a solution of 12g of 1-formyl-4-8 1-(4'-chloro[1,1']biphenyl-4-yl)propyl]piperazine in 50 ml. of 95% ethanol and 50 ml. of ethanol saturated with hydrogen chloride gas for 30 minutes. Concentrate the resulting mixture to a solid residue, take up the residue in water, filter and basify the filtrate with dilute sodium hydroxide. Filter the solid product and recrystallize from isopropyl ether-hexane to yield 1[1-(4'-chloro[1,1']biphenyl-4-yl) propyl]piperazine, m.p. 95°–97°.

In a manner similar to the techniques of the foregoing examples 5 and 6 there is also produced:

1-[1-(4'-bromo[1,1']biphenyl-4-yl)ethyl]piperazine,
1-[1-(4'-fluoro[1,1']biphenyl-4-yl)ethyl]piperazine,
1-[1-(2'-fluoro[1,1']biphenyl-4-yl)ethyl]piperazine,
1-[1-(4'-chloro[1,1']biphenyl-4-yl)butyl]piperazine,
1-[1-(4'-chloro[1,1']biphenyl-4-yl)pentyl]piperazine,
1-[1-(4'-chloro[1,1']biphenyl-4-yl)hexyl]piperazine
1-[1-(3'4'-dichloro[1,1']biphenyl-4-yl)ethyl]piperazine,
1-[1-(3',4'-difluoro[1,1']biphenyl-4-yl)ethyl]piperazine,
1-[1-(2',4'-difluoro[1,1']biphenyl-4-yl)ethyl]piperazine,
1-[1-(4'-difluoromethyl[1,1']biphenyl-4-yl)ethyl]piperazine,
1-[1-(4'-trifluoromethyl[1,1'biphenyl-4-yl)ethyl]piperazine.

EXAMPLE 7

1-Acetyl-4[1-(4'-chloro[1,1']biphenyl-4-ethyl]piperazine

Reflux a solution of 46g of 1-8 1-(4,-chloro[1,1']biphenyl-4-yl) ethyl]piperazine, 70 ml of acetic anhydride and 200 ml of anhydrous benzene for 4 hours. Concentrate the refluxed solution, in vacuo, add 300 ml of ice water and basify the mixture with dilute sodium hydroxide. Extract the crude product with ethyl acetate. Water-wash, dry (over sodium sulfate) and concentrate the organic layer to a solid residue. Recrystallize the residue from ethyl acetate to yield 1-acetyl-4[1-(4'-chloro[1,1']biphenyl-4-yl)ethyl]piperazine, m.p. 120°–121°. The hydrochloride has a m.p. of 258°–259° (ethanol-ether).

EXAMPLE 8

1-Acetyl-4[1-(4'-chloro[1,1']biphenyl-4-yl)ethyl]piperazine

With constant stirring, reflux a solution of 25.1g of 4'-chloro-4-(1-chloroethyl)[1,1']biphenyl, 51g of 1-acetyl piperazine and 400 ml of anhydrous benzene for 24 hours. Add 200 ml of water to the reaction mixture, separate the organic phase, water-wash (5 times with 200 mls of water). Dry (over sodium sulfate), concentrate (in vacuo) and recrystallize the resulting residue from ethyl acetate to obtain the desired product.

EXAMPLE 9

1-Acetyl-4[1-(4'-chloro[1,1']biphenyl-4-yl)ethyl]piperazine

To a cooled, stirred solution of 7.5g of 1-[1-(4'-chloro[1,1']biphenyl-4-yl)ethyl]piperazine in 70 ml of anhydrous benzene add 2.6g of sodium bicarbonate followed by the dropwise addition of 2.3g of acetyl chloride in 5 ml of benzene. Allow the reaction mixture to stir at room temperature for 20 hours, treat with water and separate the organic layer. Wash the benzene layer with dilute sodium bicarbonate solution, dry (over sodium sulfate), filter and concentrate (in vacuo) to a solid residue. Recrystallize from ethyl acetate.

In a manner similar to the techniques used in the procedures of examples 7, 8 and 9, there is produced the following compounds:

1-acetyl-4[1-(4'-fluoro[1,1']biphenyl-4-yl)ethyl]piperazine,
1-acetyl-4[1-(4'-bromo-[1,1']biphenyl-4-yl)ethyl]piperazine,
1-acetyl-4[1-(2'-fluoro-[1,1']biphenyl-4-yl)ethyl]piperazine,
1-acetyl-4[1-(4'-chloro-[1,1']biphenyl-4-yl)propyl]piperazine,
1-acetyl-4[1-(4'-chloro[1,1']biphenyl-4-yl)butyl]piperazine,
1-acetyl-4[1-(4'-chloro[1,1']biphenyl-4-yl)pentyl]piperazine,
1-acetyl-4[1-(4'-chloro-[1,1']biphenyl-4-yl)hexyl piperazine,
1-acetyl-4[1-(3',4'-dichloro-[1,1']biphenyl-4-yl)ethyl]piperazine,
1-acetyl-4[1-(3',4'-difluoro-[1,1']biphenyl-4-yl)ethyl]piperazine,
1-acetyl-4[1-(2',4'-difluoro-[1,1']biphenyl-4-yl)ethyl]piperazine,
1-acetyl-4[1-(4'-difluoromethyl-[1,1']biphenyl-4-yl)ethyl]piperazine,
1-acetyl-4[1-(4'-trifluoromethyl-[1,1']biphenyl-4-yl)ethyl]piperazine.

Similarly, by using the appropriate alkanoyl chloride, the 1-propionyl, 1-butyryl, 1-isovaleryl, 1-pivaloyl and the 1-cyclohexylcarbonyl analogs of the foregoing may also be prepared.

EXAMPLE 10

1-Carbethoxy-4[1-4'-chloro[1,1']biphenyl-4-yl)ethyl]piperazine

With constant stirring, heat (on a steam bath) a mixture of 1)g (0.04 mole) of 4'-chloro-4-(1-chloroethyl)[1,1']biphenyl and 30g (0.19 mole) of 1-carbethoxypiperazine for 20 hours. Treat the viscous reaction mixture with water and filter the crude product, m.p. 109°–111°. Recrystallize the solid from hexane to yield 1-carbethoxy-4-[1,1']biphenyl-4-yl]piperazine, m.p. 113°–115°.

Similarly, the 1-carbethoxy, 1-formyl, 1-methyl and other carboalkoxy and alkyl substituted piperazines may be prepared from the following compounds by substantially following the procedure set forth in the foregoing example.

4'-bromo-4-(1-chloroethyl)[1,1']biphenyl,
4'-fluoro-4-(1-chloroethyl)[1,1']biphenyl,
4'-fluoro-4-(1-chloroethyl)[1,1']biphenyl,
4'-chloro-4-(1-chlorobutyl)[1,1']biphenyl,
4'-chloro-4-(1-chloropentyl)[1,1']biphenyl,
4'-chloro-4-(1-chlorohexyl)1,1']biphenyl,
3',4'-dichloro-4-(1-chloroethyl)[1,1']biphenyl,
3',4',difluoro-4-(10chloroethyl)[1,1']biphenyl,
2',4'-difluoro-4-(1-chloroethyl)[1,1']biphenyl,
4'-difluoromethyl-4-(1-chloroethyl)[1,1']biphenyl,
4'-trifluoromethyl-4-(1-chloroethyl)[1,1']biphenyl,

EXAMPLE 11

1-Cinnamyl-4-[1-(4'-chloro[1,1']biphenyl-4-yl)ethyl]-piperazine dihydrochloride

To a stirred mixture of 8g of 1[1-(4'-chloro[1,1']biphenyl-4-yl)ethyl]piperazine, 2.7g of sodium bicarbonate in 75 ml of absolute ethanol, add in a dropwise fashion 5.25g of cinnamyl bromide. Reflux the reaction mixture for 6 hours, concentrate in vacuo, and treat with 50 ml of 10% hydrochloric acid solution. Filter the dihydrochloride and recrystallize from 80% ethanol, m.p. 273°–275°. The free base has a melting point of 108°–109° after recrystallization from acetonitrile.

Similarly by following the procedure of this example, the following compounds (both as the free base and the dihydrochloride salt) are produced:

1-cinnamyl-4-[1-(4'-bromo[1,1']biphenyl-4-yl)ethyl]piperazine,
1-cinnamyl-4-[1-(4'-fluoro[1,1']biphenyl-4-yl)ethyl]piperazine,
1-cinnamyl-4-[1-(2'-fluoro[1,1']biphenyl-4-yl)ethyl]piperazine,
1-cinnamyl-4-[1-(4'-chloro[1,1']biphenyl-4l-yl)butyl]piperazine,
1-cinnamyl-4-[1-(4'-chloro[1,1']biphenyl-4-yl)pentyl]piperazine,
1-cinnamyl-4-]1-(4'-chloro-[1,1']biphenyl-4-yl)hexyl piperazine,
1-cinnamyl-4-[1-(3',4'-dichloro[1,1']biphenyl-4-yl)ethyl]piperazine,
1-cinnamyl-4-[1-(3',4'-difluoro[1,1']biphenyl-4-yl)ethyl]piperazine, 1-cinnamyl-4-[1-(2',4'-difluoro[1,1'λ]biphenyl-4-yl)ethyl]piperazine,
1-cinnamyl-4-[1-(4'-difluoromethyl[1,1']biphenyl-4-yl)ethyl]piperazine,
1-cinnamyl-4-[1-(4'-trifluoromethyl[1,1']biphenyl-4-yl)ethyl]piperazine.

EXAMPLE 12

1-(2-hydroxyethyl)-4-[1-(4'-fluoro[1,1']biphenyl-4-yl)ethyl]piperazine

With stirring, heat (on a steam bath) a mixture of 13g of 4'-fluoro-4-(1-chloroethyl)[1,1']biphenyl and 20g of 1-(2-hydroxyethyl piperazine for twenty hours. Treat the reaction mixture with 200 ml of water, filter and wash the solid with water to yield 1-(2-hydroxyethyl)-4-[1-(4'-fluoro[1,1']biphenyl-4-yl)ethyl]piperazine: m.p. 120°–123°. Recrystallize the product from acetonitrile, m.p. of 122°–123°.

In a similar manner, there is produced the following compounds: 1-(2-hydroxyethyl)-4-[1,1']biphenyl-4-yl)ethyl]piperazine, 1-(2-hydroxyethyl)-4-[1-(4'-fluoro[1,1'λ]biphenyl-4-yl)ethyl]piperazine
1-(2-hydroxyethyl)-4-[1-(2'-fluoro[1,1']biphenyl-4-yl)ethyl]piperazine,
1(2-hydroxyethyl)-4-[1-(4'-chloro[1,1']biphenyl-4-yl)butyl]piperazine,
1-(2-hydroxyethyl)-4-[1-(4'-chloro[1,1']biphenyl-4-yl)pentyl]piperazine,
1-(2-hydroxyethyl)-4-[1-(4'-chloro[1,1']biphenyl-4-yl)hexyl]piperazine,
1-(2-hydroxyethyl)-4-[1-(3'4'-dichloro[1,1']biphenyl-4-yl)ethyl]piperazine,
1-(2-hydroxyethyl)-4-[1-(3'4'-difluoro[1,1']biphenyl-4-yl)ethyl]piperazine,
1-(2-hydroxyethyl)-4-[1-(2',4'-difluoro[1,1']biphenyl-4-yl)ethyl]piperazine,
1-(2-hydroxyethyl)-4-[1-(4'-difluoromethyl[1,1']biphenyl-4-yl)ethyl]piperazine,
1-(2-hydroxyethyl)-4-[1-(4'-trifluoromethyl[1,1']biphenyl-4-yl)ethyl]piperazine.

EXAMPLE 13

1-(2-methoxyethyl)-4-[1-(4'-fluoro[1,1']biphenyl-4-yl)ethyl]piperazine

Reflux a mixture containing 5g of 1-(2-hydroxyethyl-4-[1-(4'-fluoro[1,1']biphenyl-4-yl)ethyl]piperazine and 25 ml of thionyl chloride for thirty minutes. Concentrate the resulting mixture and triturate the solid residue with ether. Filter, and without further purification add, in a portionwise fashion, the so-obtained crude chloride dihydrochloride to a stirred solution of sodium methylate (10.5g of sodium dissolved in 200 ml of methanol). Reflux the reaction mixture for one hour, concentrate in vacuo and treat the residue with water. Filter and dry the solid product, and recrystallize from petroleum ether, m.p. 61°–62°. The dihydrochloride salt melts at 247°–248° (from ethanol).

Similarly, the following compounds may also be prepared by following the techniques of this example.

1-(2-methoxyethyl)-4-[1-(4'-bromo[1,1']biphenyl-4-yl)ethyl]piperazine,
1-(2-methoxyethyl)-4-[1-(4'-fluoro[1,1']biphenyl-4-yl)ethyl]piperazine,
1-(2-methoxyethyl)-4-[1-(2'-fluoro[1,1']biphenyl-4-yl)ethyl]piperazine,
1-(2-methoxyethyl)-4-[1-(4'-chloro[1,1']biphenyl-4-yl)butyl]piperazine,
1-(2-methoxyethyl)-4-[1-(4'-chloro[1,1']biphenyl-4-yl)pentyl]piperazine,
1-(2-methoxyethyl)-4-[1-(4'-chloro[1,1']biphenyl-4-yl)hexyl]piperazine,
1-(2-methoxyethyl)-4-[1-(3'4'-dichloro[1,1']biphenyl-4-yl)ethyl]piperazine,
1-(2-methoxyethyl)-4-[1-(3',4'-difluoro[1,1']biphenyl-4-yl)ethyl]piperazine,
1-(2-methoxyethyl)-4-[1-(2',4'-difluoro[1,1']biphenyl-4-yl)ethyl]piperazine,
1-(2-methoxyethyl)-4-[1-(4'-difluoromethyl[1,1']biphenyl-4-yl)ethyl]piperazine, 1-(2-methoxyethyl)-4-[1-(4'-trifluoromethyl[1,1']biphenyl-4-yl)ethyl]piperazine.

It is obvious to one skilled in the art that the compounds of this invention may be produced as racemic mixtures of their dextrorotary and levorotary isomers, whose separation may be effected by the usual well known techniques such as by the fractional crystallization of salts of optically active acids. Both of the optically active isomers, as well as the racemic mixtures thereof, are fully contemplated within the scope of this invention.

The compounds of this invention have the applied use characteristics of exerting an anti-inflammatory effect in mammals which is useful in the treatment of arthritis. In testing the compounds of this invention in the adjuvant-induced polyarthritic rat (AAR) (which mimics rheumatoid arthritis in terms of its pathology and the classes of drugs which suppress the symptoms of this disease), they are found to possess significant anti-inflammatory activity. When tested in the Vitamin E paw (i.e., a model of chronic non-immunologically induced inflammation) the compounds also have been found to be very active in their anti-inflammatory activity. Additionally, the compounds of this invention have been found to possess an immunological component to its mode of action. Further, the compounds have been found not to have the ulcerogenic side effects normally associated with non-steroidal anti-inflammatory agents. They have also been found not to possess the harmful effect on the blood system (i.e. they have no effect on circulating white blood cells) such as is standard for potent immunosuppressants. Thus, the compounds have a favorable biological profile when compared to other non-steroidal anti-inflammatory agents useful in the treatment of arthritis and other disease states due to inflammation.

Based upon the aforementioned and other relevant assay methodology, as well as by comparison with anti-inflammatory agents known to be useful in the treatment of arthritis, it is to be found that the compounds of this invention are useful for the treatment of this disease state by administering said compounds within a dose range of 0.5–50 milligrams per kilogram of body weight per day, administered in single or divided doses.

As is well known in the art certain members of a large class of therapeutically useful compounds have better biological profiles than that of its other members. In this class of compounds, those compounds wherein X and Y are fluoro or chloro are particularly useful, both as to mono and disubstituted compounds. Those compounds wherein $R^1$ is representative of acyl or acyloxy alkyl are also useful, particularly when acyl is representative of acetyl or pivaloyl. Preferably R is methyl.

In their function as therapeutically useful compounds, it is advantageous to administer the compounds to the host animal in admixture with an acceptable pharmaceutical carrier suitable for enteral or parenteral administration, said carrier constituting a major portion of the admixture. Such preparations may be in such forms, as for example, tablets, capsules and suppositories, or in liquid forms as for example, elixirs, emulsions and injectables. In the formulation of pharmaceutical preparations there can be employed such substances which do not react with the active substance as for example, water, gelatin, lactose, starches, magnesium stearate, calcium carbonate, talc, vegetable oils, benzyl alcohols, gums, polyalkylene glycols, petroleum jelly and the like. The active ingredient of such pharmaceutical preparations is preferably present in the preparation in such proportions by weight the the proportion by weight in the active ingredient to be administered lies between 0.1% and 50%.

TABLET FORMULATION

The following formulation provides for the manufacture of 1,000 tablets:

|   |   | Grams |
|---|---|---|
| (1) | 1-Acetyl-4[1-(4'-Chloro[1,1']biphenyl-4-yl)ethyl]piperazine | 25 |
| (2) | Lactose, U.S.P. | 181 |
| (3) | Corn starch, U.S.P. | 92.5 |
| (4) | Magnesium stearate | 1.5 |

Thoroughly granulate a mixture of 92.5 g. of corn starch and the lactose with a paste prepared by dissolving 20 mg. of corn starch in 100 ml. of hot distilled water. Dry the resulting granulation at 40°–45° C. and pass it through a No. 16 mesh screen. To the dried, screened granulation add a blended mixture of the active ingredient (1) and the magnesium stearate. Thoroughly blend and then press into tablets of 300 mg. each.

CAPSULE FORMULATION

The following formulation provides for the manufacture of 1,000 capsules:

|   |   | Grams |
|---|---|---|
| (1) | 1-Acetyl-4[1-(4'-Chloro[1,1']biphenyl-4-yl)ethyl]piperazine | 25 |
| (2) | Lactose | 273.5 |
| (3) | Magnesium stearate | 1.5 |

Mix active ingredient (1) with the lactose and blend in the magnesium stearate. Fill hard gelatin capsules with 300 mg. each of the blended mixture to produce capsules containing 25 mg. of 1-Acetyl-4[1-4'-Chloro[1,1'λ]biphenyl-4-yl)ethyl]piperazine.

I claim:

1. A compound of the formula:

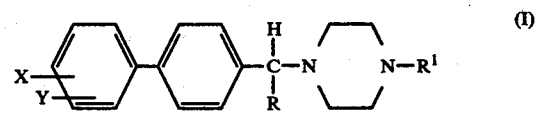

or the pharmaceutically acceptable acid addition salts thereof, wherein X is halogeno, difluoromethyl or trifluoromethyl, Y is hydrogen, halogeno, difluoromethyl, or trifluoromethyl, R is lower alkyl, $R^1$ is hydrogen, carboloweralkoxy, hydroxyloweralkyl, loweralkoxyloweralkyl, acyl or acyloxyloweralkyl, said acyl moieties being derived from monobasic carboxylic acids having up to 14 carbon atoms.

2. A compound of claim 1 wherein X is halogen, Y is hydrogen, and $R^1$ is acyl.

3. A compound of claim 1 wherein X and Y are halogen, and $R^1$ is acyl.

4. A compound of claim 1 wherein X and Y are fluoro, $R^1$ is acetyl and R is methyl.

5. A compound of claim 1 wherein X is halogen, Y is hydrogen and $R^1$ is hydrogen.

6. A compound of claim 1 wherein X and Y are halogeno and $R^1$ is formyl.

7. A compound of claim 1 wherein X and Y are halogeno and R¹ is carboloweralkoxy.

8. A compound of claim 1 wherein X and Y are halogeno and R¹ is hydroxyloweralkyl.

9. A compound of claim 1 wherein X and Y are halogeno and R¹ is acyloxyloweralkyl.

10. A compound of claim 2, wherein X is chloro and R¹ is acetyl.

11. A compound of claim 2, wherein X is chloro and R¹ is pivaloyl.

12. A compound of claim 3 wherein X and Y are fluoro and R¹ is acetyl.

13. A compound of claim 1, said compound being 1-acetyl-4-[1-(4'-chloro[1,1']biphenyl-4-yl)ethyl]piperazine.

14. A method for treating inflammation which comprises administering to a mammal suffering from inflammation a therapeutically effective quantity of a compound of the formula:

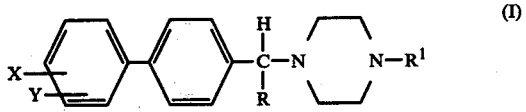

and the therapeutically acceptable acid addition salts thereof wherein X is halogeno, difluoromethyl or trifluoromethyl, Y is hydrogen, halogeno, difluoromethyl, or trifluoromethyl, R is lower alkyl, R¹ is hydrogen, formyl, carboloweralkoxy, hydroxyloweralkyl, loweralkoxyloweralkyl, acyl or acyloxyloweralkyl, said acyl moieties being derived from monobasic carboxylic acids having up to 14 carbon atoms.

* * * * *